United States Patent [19]

Morisawa et al.

[11] 4,421,766
[45] Dec. 20, 1983

[54] METHOD OF PRESERVING ORGANIC MATERIALS FROM FUNGAL ATTACK AND A COMPOSITION FOR USE IN SUCH A METHOD

[75] Inventors: Yasuhiro Morisawa; Kiyoshi Konishi; Mitsuru Kataoka, all of Hiromachi, Japan

[73] Assignee: Sankyo Co., Ltd., Tokyo, Japan

[21] Appl. No.: 338,141

[22] Filed: Jan. 8, 1982

[30] Foreign Application Priority Data

Jan. 13, 1981 [JP] Japan .................................. 56-3364

[51] Int. Cl.³ ...................... A01N 37/02; A01N 37/06
[52] U.S. Cl. .................................................. 424/311
[58] Field of Search ........................................ 424/311

[56] References Cited

PUBLICATIONS

Chemical Abstracts 64:6475c (1966).
Chemical Abstracts 95:61538q (1981).

Primary Examiner—Stanley J. Friedman
Attorney, Agent, or Firm—Frishauf, Holtz, Goodman & Woodward

[57] ABSTRACT

A variety of organic materials susceptible to fungal attack (especially wood and wood-based materials) can be protected from such attack and fungi growing on such materials can be eradicated by treating them, e.g. by applying to the surfaces or impregnating, with one or more compounds of formula (I):

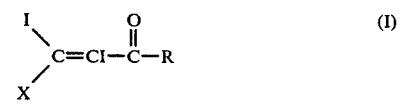

(wherein X represents a halogen atom and R represents a hydroxy group, an alkoxy gorup, a substituted or unsubstituted phenoxy group, an amino group, a mono- or di- alkylamino group, a phenylamino or benzylamino group which is unsubstituted or has one or two substituents on the benzene ring of the phenyl or benzyl moiety, or a 3-halo-2,3-diiodoallyloxy group). An anti-fungal composition contains one or more of these compounds in admixture with a carrier or adjuvant.

12 Claims, No Drawings

METHOD OF PRESERVING ORGANIC MATERIALS FROM FUNGAL ATTACK AND A COMPOSITION FOR USE IN SUCH A METHOD

BACKGROUND TO THE INVENTION

The present invention relates to a method of preserving organic materials from fungal attack by applying to or incorporating into the materials one or more of certain trihaloacrylic acid derivatives. The invention also provides a composition for use in such a method including one or more of the trihaloacrylic acid derivatives.

Most organic materials are susceptible, to some degree, to attack by a variety of natural pests, especially fungi. Susceptible materials include building materials (such as wood) and industrial materials (such as wet pulp, paper, straw mats, fibres, leathers, adhesives, paints, synthetic resins, wood and wood-containing or wood-based materials). The growth of undesirable fungi on these materials can lead not only to contamination but also to structural damage and the eradication of fungi, once established, can prove extremely difficult and often highly expensive. Preservation of such materials from fungal attack is also difficult and expensive. There is, therefore, a continuing need for new compounds to preserve organic materials from fungal attack and to eradicate already established fungal colonies.

A variety of trihaloallyl derivatives have been found to be valuable anti-fungal agents. Also, triiodoacrylic acid and certain alkyl esters thereof have been disclosed in Chemical Pharmaceutical Bulletin, 14, 1122 (1966), but no use for these compounds has been suggested.

BRIEF SUMMARY OF INVENTION

We have now surprisingly discovered that certain trihaloacrylic acids and derivatives, including esters, thereof are valuable anti-fungal agents. Accordingly, the present invention provides a method of protecting degradeable organic materials from fungal attack by applying to or admixing with said material a compound of formula (I):

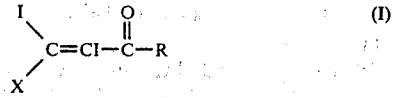

wherein:

X represents a chlorine, bromine or iodine atom; and

R represents a hydroxy group, an alkoxy group, a phenoxy group which is unsubstituted or has one or two alkyl, alkoxy or halogen substituents, an amino group, an alkylamino group, a dialkylamino group, a phenylamino group which is unsubstituted or has one or two alkyl, alkoxy or halogen substituents on the benzene ring, a benzylamino group which is unsubstituted or has one or two alkyl, alkoxy or halogen substituents on the benzene ring, or a group of formula

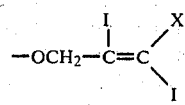

(in which X is as defined above).

The invention also provides a preservative and anti-fungal composition containing an anti-fungal agent in association with a carrier or adjuvant wherein the anti-fungal agent is a compound of formula (I), as defined above.

DETAILED DESCRIPTION OF INVENTION

In the compounds of formula (I) where R represents an alkoxy group, this may be a straight or branched chain alkoxy group and is preferably such a group having from 1 to 6 carbon atoms, for example a methoxy, ethoxy, propoxy, isopropoxy, butoxy, pentyloxy or hexyloxy group.

Where R represents a phenoxy group, this may be an unsubstituted phenoxy group or it may be a substituted phenoxy group having one or two substituents. The substituents, which may be the same or different, are selected from: alkyl groups, preferably alkyl groups having from 1 to 4 carbon atoms (especially the methyl group); alkoxy groups, preferably alkoxy groups having from 1 to 4 carbon atoms (especially the methoxy group); and halogen atoms (especially chlorine or bromine atoms). Examples of such phenoxy groups include the phenoxy, o-methylphenoxy, m-methylphenoxy, p-methylphenoxy, 2,4-dimethylphenoxy, p-methoxyphenoxy, o-chlorophenoxy, m-chlorophenoxy, p-chlorophenoxy, o-bromophenoxy, m-bromophenoxy, p-bromophenoxy, 2,4-dichlorophenoxy, 2,3-dichlorophenoxy and 3,5-dichlorophenoxy groups.

Where R represents an alkylamino group, the alkyl group may be a straight or branched chain group preferably having from 1 to 6 carbon atoms. Examples of such groups include the methylamino, ethylamino, propylamino, isopropylamino, butylamino, pentylamino and hexylamino groups. Where R represents a dialkylamino group, the alkyl groups (which may be the same or different, preferably the same) preferably have from 1 to 4 carbon atoms. Examples include the dimethylamino and diethylamino groups.

Where R represents a phenylamino group, the phenyl group may be unsubstituted or may have one or two substituents selected from: alkyl groups, preferably having from 1 to 4 carbon atoms (especially the methyl group); alkoxy groups, preferably having from 1 to 4 carbon atoms (especially the methoxy group); and halogen atoms (especially chlorine and bromine atoms). Examples of such phenylamino groups include the anilino, o-toluidino, m-toluidino, p-toluidino, o-anisidino, m-anisidino, p-anisidino, o-chlorophenylamino, m-chlorophenylamino, p-chlorophenylamino, o-bromophenylamino, m-bromophenylamino, p-bromophenylamino, 2,3-dichlorophenylamino, 2,4-dichlorophenylamino, 2,5-dichlorophenylamino and 3,4-dichlorophenylamino groups.

Where R represents a benzylamino group, the benzyl group may be unsubstituted or may have in its benzene ring one or two substituents selected from: alkyl groups, preferably having from 1 to 4 carbon atoms (especially the methyl group); alkoxy groups, preferably having from 1 to 4 carbon atoms (especially the methoxy group); and halogen atoms (especially chlorine and bromine atoms). Examples of such benzylamino groups include the benzylamino, o-methylbenzylamino, m-methylbenzylamino, p-methylbenzylamino, o-methoxybenzylamino, m-methoxybenzylamino, p-methoxybenzylamino, o-chlorobenzylamino, m-chlorobenzylamino, p-chlorobenzylamino, o-bromobenzylamino, m-bromobenzylamino, p-bromobenzylamino, 2,3-dichlorobenzylamino, 2,4-dichlorobenzylamino, 2,5- dichlorobenzylamino and 3,4-dichlorobenzylamino groups.

Where R represents a trihaloallyloxy group, that is to say a group of formula

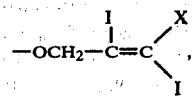

this is preferably a 2,3,3-triiodoallyloxy or 3-bromo-2,3-diiodoallyloxy group.

Specific examples of compounds of formula (I) are listed below. The compounds are hereinafter referred to by the numbers assigned to them in this list.
1. Methyl 2,3,3-triiodoacrylate
2. Ethyl 2,3,3-triiodoacrylate
3. Propyl 2,3,3-triiodoacrylate
4. Isopropyl 2,3,3-triiodoacrylate
5. Butyl 2,3,3-triiodoacrylate
6. Hexyl 2,3,3-triiodoacrylate
7. Phenyl 2,3,3-triiodoacrylate
8. o-Methylphenyl 2,3,3-triiodoacrylate
9. m-Methylphenyl 2,3,3-triiodoacrylate
10. p-Methylphenyl 2,3,3-triiodoacrylate
11. 2,4-Dimethylphenyl 2,3,3-triiodoacrylate
12. p-Methoxyphenyl 2,3,3-triiodoacrylate
13. o-Chlorophenyl 2,3,3-triiodoacrylate
14. m-Chlorophenyl 2,3,3-triiodoacrylate
15. p-Chlorophenyl 2,3,3-triiodoacrylate
16. p-Bromophenyl 2,3,3-triiodoacrylate
17. 2,4-Dichlorophenyl 2,3,3-triiodoacrylate
18. 2,3-Dichlorophenyl 2,3,3-triiodoacrylate
19. 3,5-Dichlorophenyl 2,3,3-triiodoacrylate
20. Methyl 3-bromo-2,3-diiodoacrylate
21. Ethyl 3-bromo-2,3-diiodoacrylate
22. Propyl 3-bromo-2,3-diiodoacrylate
23. Butyl 3-bromo-2,3-diiodoacrylate
24. Phenyl 3-bromo-2,3-diiodoacrylate
25. o-Methylphenyl 3-bromo-2,3-diiodoacrylate
26. m-Methylphenyl 3-bromo-2,3-diiodoacrylate
27. p-Methylphenyl 3-bromo-2,3-diiodoacrylate
28. 2,4-Dimethylphenyl 3-bromo-2,3-diiodoacrylate
29. p-Methoxyphenyl 3-bromo-2,3-diiodoacrylate
30. o-Chlorophenyl 3-bromo-2,3-diiodoacrylate
31. p-Chlorophenyl 3-bromo-2,3-diiodoacrylate
32. 2,4-Dichlorophenyl 3-bromo-2,3-diiodoacrylate
33. 2,3,3-Triiodoacrylic acid
34. 3-Bromo-2,3-diiodoacrylic acid
35. 2,3,3-Triiodoacrylamide
36. 3-Bromo-2,3-diiodoacrylamide
37. N-Methyl-2,3,3-triiodoacrylamide
38. N-Ethyl 2,3,3-triiodoacrylamide
39. N-Propyl-2,3,3-triiodoacrylamide
40. N-Butyl-2,3,3-triiodoacrylamide
41. N-Hexyl-2,3,3-triiodoacrylamide
42. N-Phenyl-2,3,3-triiodoacrylamide
43. N-(o-Methylphenyl)-2,3,3-triiodoacrylamide
44. N-(m-Methylphenyl)-2,3,3-triiodoacrylamide
45. N-(p-methylphenyl)-2,3,3-triiodoacrylamide
46. N-(m-Methoxyphenyl)-2,3,3-triiodoacrylamide
47. N-(p-Methoxyphenyl)-2,3,3-triiodoacrylamide
48. N-(o-Chlorophenyl)-2,3,3-triiodoacrylamide
49. N-(p-Chlorophenyl)-2,3,3-triiodoacrylamide
50. N-(2,4-Dichlorophenyl)-2,3,3-triiodoacrylamide
51. N-(2,3-Dichlorophenyl)-2,3,3-triiodoacrylamide
52. N-(2,5-Dichlorophenyl)-2,3,3-triiodoacrylamide
53. N-(3,4-Dichlorophenyl)-2,3,3-triiodoacrylamide
54. N-Methyl-3-bromo-2,3-diiodoacrylamide
55. N-Ethyl-3-bromo-2,3-diiodoacrylamide
56. N-Propyl-3-bromo-2,3-diiodoacrylamide
57. N-Butyl-3-bromo-2,3-diiodoacrylamide
58. N-Phenyl-3-bromo-2,3-diiodoacrylamide
59. N-(o-Methylphenyl)-3-bromo-2,3-diiodoacrylamide
60. N-(m-Methylphenyl)-3-bromo-2,3-diiodoacrylamide
61. N-(p-Methylphenyl)-3-bromo-2,3-diiodoacrylamide
62. N-(o-Chlorophenyl)-3-bromo-2,3-diiodoacrylamide
63. N-(p-Chlorophenyl)-3-bromo-2,3-diiodoacrylamide
64. N-(2,4-Dichlorophenyl)-3-bromo-2,3-diiodoacrylamide
65. N-Benzyl-2,3,3-triiodoacrylamide
66. N-(o-Methylbenzyl)-2,3,3-triiodoacrylamide
67. N-(m-Methylbenzyl)-2,3,3-triiodoacrylamide
68. N-(p-Methylbenzyl)-2,3,3-triiodoacrylamide
69. N-(o-Chlorobenzyl)-2,3,3-triiodoacrylamide
70. N-(m-Chlorobenzyl)-2,3,3-triiodoacrylamide
71. N-(p-Chlorobenzyl)-2,3,3-triiodoacrylamide
72. N-(2,4-Dichlorobenzyl)-2,3,3-triiodoacrylamide
73. N-Benzyl-3-bromo-2,3-diiodoacrylamide
74. N-(o-Methylbenzyl)-3-bromo-2,3-diiodoacrylamide
75. N-(m-Methylbenzyl)-3-bromo-2,3-diiodoacrylamide
76. N-(p-Methylbenzyl)-3-bromo-2,3-diiodoacrylamide
77. N-(o-Chlorobenzyl)-3-bromo-2,3-diiodoacrylamide
78. N-(m-Chlorobenzyl)-3-bromo-2,3-diiodoacrylamide
79. N-(p-Chlorobenzyl)-3-bromo-2,3-diiodoacrylamide
80. N-(2,4-Dichlorobenzyl)-3-bromo-2,3-diiodoacrylamide
81. Methyl 3-chloro-2,3-diiodoacrylate
82. Ethyl 3-chloro-2,3-diiodoacrylate
83. Propyl 3-chloro-2,3-diiodoacrylate
84. Phenyl 3-chloro-2,3-diiodoacrylate
85. N-Methyl-3-chloro-2,3-diiodoacrylamide
86. 2',3',3'-Triiodoallyl 2,3,3-triiodoacrylate
87. 2',3',3'-Triiodoallyl 3-bromo-2,3-diiodoacrylate
88. 3'-Bromo-2',3'-diiodoallyl 2,3,3-triiodoacrylate
89. 3'-Bromo-2',3'-diiodoallyl 3-bromo-2,3-diiodoacrylate Of the compounds listed above, we particularly prefer to use Compounds No. 1, 2, 7, 15, 20, 21, 23, 24, 31, 33, 34, 36, 39, 54, 55 and 73.

Compounds No. 1, 2 and 33 are disclosed in Chemical Pharmaceutical Bulletin, 14, 1122 (1966), referred to above.

Compounds of formula (I) in which R represents a hydroxy group, that is to say the 3-halo-2,3-diiodoacrylic acids, may be prepared by reacting the corresponding 3-halopropiolic acid with iodine. The remaining compounds of formula (I) may be prepared by reacting this 3-halo-2,3-diiodoacrylic acid with thionyl chloride, to give the acid chloride, and then contacting this acid chloride with a compound of formula R'H (in which R' represents any one of the groups defined for R except a hydroxy group). Alternatively, the compound of formula (I) in which R represents a methoxy group, that is to say the methyl 3-halo-2,3diiodoacrylates, may be prepared by reacting the corresponding 3-halo-2,3-diiodoacrylic acid with diazomethane by conventional means. These reactions are illustrated in the following reaction scheme:

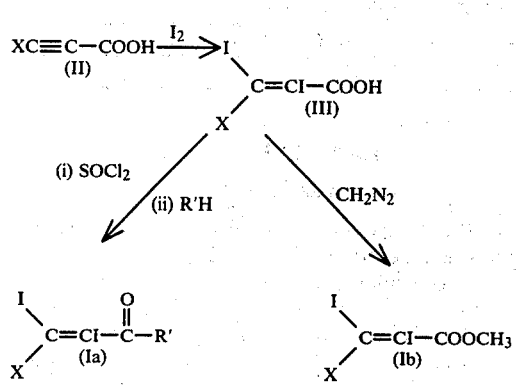

Materials which may be preserved and protected from the harmful effects of fungal attack by means of the compounds of formula (I) include, in particular, woody materials and plywood, as well as a variety of industrial materials, such as wet pulp, paper, mats, fibres, leather, adhesives, paints and synthetic resins. However, in general, any organic material susceptible to deterioration as a result of fungal attack may be protected by the compounds of formula (I).

Various fungi are known to grow on industrial materials. Examples include fungi of the genera Penicillium, Aspergillus, Rhizopus, Chaetomium, Cladosporium, Fusarium and Aureobasidium, and others, for example those of the genus Trichoderma and wood-staining fungi, are also known. However, the fungi susceptible to the compounds of the invention are not limited to these particular genera of fungi. As for wood preservation, the compounds of formula (I) can be used to prevent damage caused by the fungi classified as "wood rotting" or "wood soft rotting" fungi.

The compounds of formula (I) may be formulated with a carrier or, if desired, with other adjuvants and may be prepared in forms commonly employed for preservative and anti-fungal uses, such as oil-soluble preparations, emulsions, pastes, powders, wettable powders, aerosols or paints. Suitable carriers include: inert solid carriers, such as clay, talc, bentonite, kaolin, silicic anhydride, calcium carbonate and wood meal; liquid carriers, such as kerosene, ligroin, the xylenes, methylnaphthalene, dimethylformamide and dimethyl sulphoxide; and vapour carriers, such as nitrogen gas, dimethyl ether, the vapourizable fluoro carbons and chlorofluorocarbons (such as those sold under the Trade Mark 'Freon') and monomeric vinyl chloride. In order to improve the properties of the composition and/or to enhance its anti-fungal and preservative effects, any suitable auxiliary agent may be employed in addition to these carriers. Examples include anionic, cationic and non-ionic surface active agents and various high molecular weight compounds, such as methylcellulose, vinyl acetate resins and sodium alginate.

It is, of course, also possible to enhance the anti-fungal or preservative effect of the composition by using the compounds of formula (I) in admixture with other anti-fungal or preservative agents, such as: 2-(4-thiazolyl)benzimidazole (thiabendazole); N,N-dimethyl-N'-dichlorofluoromethylthio-N'-phenylsulphamide (Dichlofluanid); 4-chlorophenyl-3'-iodopropargylformal; halogenated phenols, such as trichlorophenol or tribromophenol; trialkyltin or triaryltin compounds, such as bis-tributyltin oxide, tributyltin phthalate or triphenyltin hydroxide; N-nitroso-N-cyclohexylamine metal salts, e.g. the aluminium salt; xyligen-B; and the benzanilides, such as 4'-chlorobenzanilide. The compounds may also be formulated with insecticides, such as organic phosphates (e.g. phoxim), pyrethroids (e.g. permethrin), carbamates (e.g. baygon) and organic chlorides (e.g. chlordane), as well as synergists and perfume.

Where the compound of formula (I) is employed in the form of a composition in admixture with one or more other materials, the proportion of the compound may vary over a wide range, depending upon the nature of the composition and the materials to be treated. In general, the compound of formula (I) constitutes from 0.01 to 95% by weight, preferably from 0.5 to 70% by weight, of the composition.

The preservative and anti-fungal composition of the invention may be applied to wood or wood-based materials by various means, e.g. by dipping, coating, spraying or impregnation. The composition can also be used, together with an adhesive, for the treatment of such materials as plywoods, hardboards and particle boards.

The preparation of the compounds of formula (I) is illustrated by the following Preparations 1 to 4, whilst the activity of the compounds is illustrated by following Examples 1 and 2 and compositions of the invention are illustrated by Examples 3 to 8.

PREPARATION 1

3-Bromo-2,3-diiodoacrylic acid

A solution of sodium hypobromite (Solution A) was prepared by adding 20.8 g of bromine, with cooling, to 70 ml of an aqueous solution containing 11.2 g of sodium hydroxide. Meanwhile, SolutioN B was prepared by adding 5.3 g of sodium carbonate to 50 ml of an aqueous solution containing 7.0 g of propiolic acid.

Solution A was then added to Solution B and the mixture was allowed to react for 30 minutes. The mixture was then cooled and its pH value was adjusted to 3.0 by the addition of concentrated hydrochloric acid. The mixture was then extracted with ethyl acetate. The extract was washed with water and dried, and then the solvent was distilled off, to give an oily substance. This oily substance was crystallized from a small amount of ethyl acetate, to afford 7 g of 3-bromopropiolic acid (melting at 84°–85° C.).

2.3 g of this 3-bromopropiolic acid were dissolved in carbon tetrachloride, and then 3.8 g of iodine were added and the resulting mixture was stirred, whilst irradiating it with infrared radiation, for 4 hours. The crystals which precipitated were recrystallized from water, giving 4.0 g of the title compound, melting at 157°–158° C.

PREPARATION 2

Methyl 3-bromo-2,3-diiodoacrylate 0.5 g of 3-bromo-2,3-diiodoacrylic acid was dissolved in 20 ml of diethyl ether. A solution of diazomethane in diethyl ether was then added until nitrogen gas was no longer produced, whereupon the mixture was left to stand for 15 minutes. The diethyl ether was distilled off, giving 0.50 g of the desired compound as an oil.

Infrared Absorption Spectrum (liquid)$\nu_{max}$cm$^{-1}$: 1730.

Elemental Analysis: Calculated for $C_4H_3BrI_2O_2$: C, 11.53%; H, 0.72%; Br, 19.17%; I, 60.90%. Found: C, 11.41%; H, 0.69%; Br, 19.30%; I, 60.79%.

PREPARATION 3

N-Ethyl-3-bromo-2,3-diiodoacrylamide

A mixture of 2.5 g of 3-bromo-2,3-diiodoacrylic acid and 10 ml of thionyl chloride was heated under reflux for 30 minutes, after which the excess thionyl chloride was distilled off under reduced pressure, to give 2.6 g of 3-bromo-2,3-diiodoacryloyl chloride, in the form of an oil.

1 g of this acid chloride was then dissolved in 20 ml of benzene, and then 0.45 g of a 70% W/W aqueous solution of ethylamine was added and the mixture was stirred at room temperature for 1 hour. The benzene was distilled off and water was added to the residue, producing crystals, which were recrystallized from ethyl acetate, to afford 0.85 g of the title compound, melting at 154°–155° C.

Infrared Absorption Spectrum (Nujol-Trade Mark)$\nu_{max}$cm$^{-1}$: 1630.

PREPARATION 4

Phenyl 2,3,3-triiodoacrylate

A solution of 0.3 ml of thionyl chloride in 2 ml of benzene was added dropwise to a mixture of 0.3 g of triiodoacrylic acid, 0.3 ml of pyridine and 3 ml of benzene. The mixture was then stirred at room temperature for 45 minutes, after which the solvent was distilled off under reduced pressure. 5 ml of benzene and 0.3 ml of pyridine were added to the resulting residue, and then 0.3 g of phenol was added, with ice-cooling, after which the mixture was stirred at room temperature for 2 hours. At the end of this time, the reaction mixture was poured into an ice-cooled dilute solution of hydrochloric acid and then extracted with diethyl ether. The extract was washed, in turn, with a saturated aqueous solution of sodium bicarbonate, water and then a saturated aqueous solution of sodium chloride. The resulting solution was dried over anhydrous sodium sulphate and then the solvent was distilled off under reduced pressure. The resulting residue was purified by column chromatography through silica gel eluted with a 100:12 by volume mixture of hexane and ethyl acetate, to give 0.18 g of the title compound, melting at 83°–84.5° C.

By following the procedures described in the above Preparations, the following compounds (identified by the numbers assigned to them in the list hereinbefore) were also prepared. Where the product was a solid, its melting point is given; where it was an oil, its Rf value (obtained by thin layer chromatography on silica gel developed with a 5:1 by volume mixture of hexane and ethyl acetate) is given:

| Compound No. | M.P. (°C.) or Rf value |
|---|---|
| 1 | 82–83 |
| 2 | 57–58 |
| 15 | 106–107 |
| 21 | oil 0.68 |
| 23 | oil 0.79 |
| 24 | oil 0.68 |
| 31 | 88–89 |
| 33 | 206–207 (with decomposition) |
| 36 | 210–211 |
| 42 | 162–164 (with decomposition) |
| 54 | 185–189 |
| 58 | 165–166 |
| 73 | 120–121 |
| 87 | 128–130 |
| 88 | 96–97 |

EXAMPLE 1

Anti-fungal activity

Each of the compounds under test was dissolved in dimethylformamide to produce a 2% w/v solution. Pieces of moso bamboo and beech sapwood were then cut to 2×2×0.2 cm to produce test samples. These test samples were then each dipped in one of the test solutions for 5 seconds, air-dried, washed with water (at a supply rate of about 2 liters/minute) for 1 hour, air-dried for 24 hours, heated at 60° C. for 24 hours and finally sterilized by dry air.

Each test sample was then tested for its resistance to fungal growth by a method based on the procedure prescribed by Japanese Industrial Standard (JIS) Z-2911. Specifically, a suspension of one of the test fungi, *Aspergillus niger* (Test fungus No. 1), *Trichoderma viride* (Test fungus No. 2), *Fusarium moniliforme* (Test fungus No. 3) and *Pullularia pullulans* (Test fungus No. 4), was innoculated into each test sample and then cultivated at 25° C. for 3 weeks in a sterile petri dish containing wet filter papers. The growth of the myceliam was examined and the results are shown in Table 1, using the following ratings:

+: no growth of fungus was observed on test sample;
±: only slight growth of fungus was observed on test sample;
−: growth of fungus was observed on test sample.

The compounds of the invention are identified in Table 1, by the numbers assigned to them in the foregoing list. Untreated control samples of the two woods were also exposed to the various fungi and the results are also shown in Table 1.

TABLE 1

| | Anti-fungal activity | | | | | | | |
|---|---|---|---|---|---|---|---|---|
| | Moso bamboo (test fungus No.) | | | | Beech (test fungus No.) | | | |
| Compound No. | 1 | 2 | 3 | 4 | 1 | 2 | 3 | 4 |
| 1 | + | + | + | + | + | + | + | + |
| 2 | + | + | + | + | + | + | + | + |
| 7 | + | ± | ± | + | + | ± | + | + |
| 15 | + | ± | + | + | + | + | + | + |
| 20 | + | + | + | + | + | + | + | + |
| 21 | + | + | + | + | + | + | + | + |
| 23 | + | + | + | + | + | + | + | + |
| 24 | + | ± | ± | + | + | + | + | + |
| 31 | + | ± | ± | ± | + | ± | + | + |
| 33 | + | + | + | + | + | + | + | + |
| 34 | + | ± | + | + | + | + | + | + |
| 39 | + | + | + | + | + | + | + | + |
| 54 | + | ± | + | + | + | ± | + | + |
| 55 | + | ± | ± | + | + | + | ± | + |
| 73 | + | ± | ± | + | + | + | + | + |
| 87 | + | + | + | + | + | + | + | + |
| 88 | + | + | + | + | + | + | + | + |
| Untreated control | − | − | − | − | − | − | − | − |

EXAMPLE 2

Wood preservative activity

This test is based upon the procedure of JIS A-9302. Each test compound was dissolved in methanol to produce a 0.1% w/v solution. Pieces of sugi sapwood were cut into test samples of dimensions 2×2×1 cm and each sample was impregnated under reduced pressure with one of the test solutions and then air-dried. After this treatment, the test samples were weathered by subjecting them twice to the following sequence of operations: leaching with water at a supply rate of about 2 liters/minute for 5 hours; air-drying for 24 hours; and heating at 60° C. for 24 hours. After this, the samples were sterilized by dry air.

The test samples thus prepared were each placed upon fungal mycelia of the lignin-decomposing fungus, *Coriolus versicolor,* or the cellulose-decomposing fungus, *Tyromyces palustris,* which had been previously incubated in a sterile petri dish containing a medium including 2% w/v malt extract, 1% w/v glucose and 0.5% w/v peptone. The samples were then subjected to forced decay by the fungi at 25° C. for 3 weeks. The growth of the mycelia on the samples and the reduction in compressive strength of the samples were determined in order to estimate the preservative activities of the compounds under test. The results are shown in Table 2, in which the preservative activity is indicated by the following ratings:

+: no fungal growth is observed on the test samples and there is no change in compressive strength;
±: a slight growth of mycelium is observed on the test samples or the compressive strength is reduced slightly;
−: growth of mycelium is observed on the test sample or its compressive strength is reduced significantly.

TABLE 2

| Compound No. | Preservative activity | |
| --- | --- | --- |
| | *Coriolus versicolor* | *Tyromyces palustris* |
| 1 | + | + |
| 2 | + | + |
| 7 | + | + |
| 15 | + | ± |
| 20 | + | + |
| 21 | + | + |
| 23 | + | + |
| 33 | + | ± |
| 36 | + | ± |
| 54 | + | + |
| 55 | + | + |
| 87 | + | + |
| 88 | + | + |
| Untreated control | − | − |

EXAMPLE 3

Emulsion 10 parts by weight of Compound No. 1 were dissolved in 40 parts by weight of dimethylformamide. 50 parts by weight of xylene and 10 parts by weight of polyoxyethylene nonylphenyl ether were added to the solution and then the mixture was thoroughly blended to give an emulsion.

This emulsion may be diluted with any desired quantity of water and applied to wood or wood-based materials by various means, e.g. by coating, dipping or spraying. The emulsion can also be used, together with an adhesive, for the treatment of such materials as plywoods, particle boards or hardboards.

EXAMPLE 4

Oil-soluble preparation 2 parts by weight of Compound No. 2 were dissolved in 2 parts by weight of dimethylformamide. 96 parts by weight of solvent naptha were then added to the solution, to give an oil-soluble preparation. This preparation can be applied to wood or wood-based materials by such means as spraying, coating, dipping or impregnation.

EXAMPLE 5

Powder 2 parts by weight of Compound No. 1 were dissolved in 10 parts by weight of acetone. 68 parts by weight of clay and 30 parts by weight of talc were then added to the solution and the mixture was thoroughly blended. The acetone was then vapourized to give a powder.

EXAMPLE 6

Wettable Powder 40 parts by weight of Compound No. 2, 56 parts by weight of clay, 3 parts by weight of sodium lauryl sulphate and 1 part by weight of polyvinyl alcohol were homogeneously blended in a mixer and then pulverized by a hammer mill to give a wettable powder.

EXAMPLE 7

Paint 10 parts by weight of Compound No. 21, 20 parts by weight of barytes powder, 10 parts by weight of a vinyl resin, 25 parts by weight of rosin and 35 parts by weight of xylene were homogeneously blended to give a paint.

EXAMPLE 8

Aerosol 2 parts by weight of Compound No. 20 and 0.5 parts by weight of a perfume were dissolved in 40 parts by weight of deodorized kerosene. The resulting solution was charged into an aerosol vessel. A valve was attached to the vessel and then 58 parts by weight of liquified petroleum gas were charged into it under pressure to give an aerosol.

We claim:

1. A method of protecting degradeable organic material from fungal attack by applying to or admixing with said material an anti-fungal effective amount of a compound of formula (I):

$$\begin{array}{c}I\\ \diagdown\\ \phantom{X}C=CI-\overset{\overset{\displaystyle O}{\|}}{C}-R\\ \diagup\\ X\end{array}\quad (I)$$

wherein: X represents a chlorine, bromine or iodine atom; and R represents a hydroxy group or a $C_1$-$C_6$ alkoxy group.

2. The method of claim 1 wherein said compound of formula (I) is methyl 2,3,3-triiodoacrylate.

3. The method of claim 1 wherein said compound of formula (I) is ethyl 2,3,3-triiodoacrylate.

4. The method of claim 1 wherein said compound of formula (I) is phenyl 2,3,3-triiodoacrylate.

5. The method of claim 1 wherein said compound of formula (I) is p-chlorophenyl 2,3,3-triiodoacrylte.

6. The method of claim 1 wherein said compound of formula (I) is methyl 3-bromo-2,3-diiodoacrylate.

7. The method of claim 1 wherein said compound of formula (I) is ethyl 3-bromo-2,3-diiodoacrylate.

8. The method of claim 1 wherein said compound of formula (I) is butyl 3-bromo-2,3-diiodoacrylate.

9. The method of claim 1 wherein said compound of formula (I) is phenyl 3-bromo-2,3-diiodoacrylate.

10. The method of claim 1 wherein said compound of formula (I) is p-chlorophenyl 3-bromo-2,3-diiodacrylate.

11. The method of claim 1 wherein said compound of formula (I) is 2,3,3-triiodoacrylic acid.

12. The method of claim 1 wherein said compound of formula (I) is 3-bromo-2,3-diiodoacrylic acid.

* * * * *